United States Patent [19]

Curtze et al.

[11] Patent Number: 4,920,222

[45] Date of Patent: Apr. 24, 1990

[54] PREPARATION OF 3,3-DIARYLACRYLIC ACID AMIDES

[75] Inventors: Jürgen Curtze, Johannisberg; Ludwig Schröder, Ingelheim, both of Fed. Rep. of Germany; Paul H. Briner, Faversham, England

[73] Assignee: Shell Internationale Research Maatschappij B.V., The Hague, Netherlands

[21] Appl. No.: 302,938

[22] Filed: Jan. 30, 1989

[30] Foreign Application Priority Data

Feb. 19, 1988 [DE] Fed. Rep. of Germany ....... 3805235

[51] Int. Cl.$^5$ .................. C07C 103/58; C07C 102/00; C07D 295/18
[52] U.S. Cl. .................................... 544/158; 544/165; 544/176; 564/149; 564/162; 564/163; 564/168; 564/171; 564/172; 564/174; 564/181; 534/558; 534/649; 534/798; 534/850; 534/860; 534/885

[58] Field of Search ........... 544/158, 165, 176; 564/149, 162, 163, 168, 172, 174, 171, 181; 534/558, 649, 798, 850, 860, 885

[56] References Cited

FOREIGN PATENT DOCUMENTS 1175830 10/1984 Canada .................. 544/176
0294907 12/1988 European Pat. Off. ............ 564/181
3536029  7/1987 Fed. Rep. of Germany ...... 544/176

OTHER PUBLICATIONS

Chem. Abstracts, vol. 107, No. 15; Abst. No. 134314s to Curtze et al.
Colwell et al., J. Med. Chem. 11, pp. 749–752 (1968).

*Primary Examiner*—Mary C. Lee
*Assistant Examiner*—Mary Sue Howard

[57] ABSTRACT

3,3-Diarylacrylic acid amides are prepared by the reaction of a benzophenone with an acetamide in the presence of a base characterized in that a sodium alcoholate is used as the base.

7 Claims, No Drawings

PREPARATION OF 3,3-DIARYLACRYLIC ACID AMIDES

The present invention relates to a process for the preparation of 3,3-diarylacrylic acid amides.

EP 0 120 321 A1, EP 0 208 999 A1 and EP 0 219 756 A1 discloses certain 3,3-diarylacrylic acid amides and various methods for the preparation of such compounds. These compounds exhibit fungicidal activity and are particularly suitable for the control of phytopathogenic fungi. EP 0 294 907 discloses a different method for the preparation of such compounds which involves the reaction of a benzophenone with an appropriate acetamide, preferably in the presence of a strong base such as potassium tert-butylate, an alkali metal hydroxide or carbonate, or tert-butyl lithium. However, the latter method generally gives yields of less than 50%.

It has now been found that a surprising yield increase to levels in excess of 90% can be obtained if a sodium tertiary alcoholate is used as the base in the method of EP 0 294 907. According to the present invention there is therefore provided a process for the preparation of a 3,3-diarylacrylic acid amide of general formula I

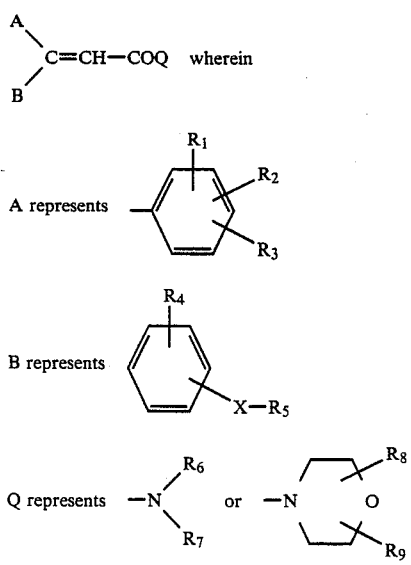

in which
$R_1$ is $C_{1-4}$alkyl, $C_{1-4}$-alkoxy, $NH_2$, $NHC_{1-4}$-alkyl, $N(C_{1-4}$-alkyl$)_2$, $C_{3-4}$-alkenyl, $C_{3-4}$-alkynyl, $C_{3-4}$ alkenyloxy, $C_{3-4}$-alkynyloxy, or $C_{3-6}$-cycloalkyl;
$R_2$ is $C_{1-4}$-alkyl, $C_{1-4}$-alkoxy or halogen;
$R_3$ is hydrogen or halogen;
$R_4$ is hydrogen, halogen, $C_{1-4}$-alkyl or $C_{1-4}$-alkoxy;
$R_5$ is hydrogen, a phenyl group optionally substituted by one or more substituents selected from $C_{1-4}$-alkyl, $C_{1-4}$-alkoxy and halogen moieties, a $C_{1-12}$ alkyl group optionally substituted by one or more halogen atoms, a $C_{3-7}$-cycloalkyl, phenylphenyl, or phenoxyphenyl group, a $C_{2-6}$-alkenyl or $C_{2-6}$-alkynyl group each optionally substituted by a phenyl group, or a naphthyl or $C_{5-8}$-cycloalkenyl group;
X is a single bond, $-O-$, $-S(O)_p-$, $-N=N-$, $-CHR_9O-$, $-OCHR_9-$, $-CHR_9S(O)_p-$, $-S(O)_pCHR_9-$ $-(CH_2)_n-$, $-HC=CH-$, or $-C\equiv C-$;
$R_6$ is $C_{1-4}$-alkyl, $C_{3-7}$-cycloalkyl, benzyl, $C_{3-4}$-alkenyl or $C_{3-4}$-alkynyl;
$R_7$ is $C_{1-4}$ alkyl;
$R_8$ is hydrogen, $C_{1-4}$-alkyl or $C_{1-4}$-alkoxy;
$R_9$ is hydrogen or $C_{1-4}$-alkyl;
p is 0, 1 or 2; and
n is an integer from 1 to 10
by reacting a benzophenone of formula II

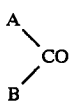

in which A and B have the meanings given above, with an acetamide of formula III $$CH_3COQ \qquad (III)$$

in which Q has the meaning given above, in the presence of a base characterised in that the base employed is a sodium tertiary alcoholate.

The alcoholate may be derived from any tertiary alcohol but good results have been obtained with a compound of formula IV $$(R)_3C-OH \qquad (IV)$$

wherein each R is independently an alkyl group of 1 to 4 carbon atoms. Preferably two of the groups R are methyl groups and the remaining R is a methyl, ethyl, propyl or butyl group. Excellent results in terms of yield of compounds of formula I have been obtained with alcoholates derived from amyl alcohol and butyl alcohol. The alcoholate may be prepared in situ or added as such and may be prepared by known methods e.g. by the reaction of sodium hydride with the tertiary alcohol in the presence of an inert solvent such as toluene.

The process according to the invention is carried out in the presence of inert solvents such as toluene, benzene, diethyl ether, diglyme, tetrahydrofuran, N,N-dimethyl formamide. Also an excess of one reaction component may serve as solvent. According to the reactivity of the components, the reaction may be carried out with cooling, at room temperature, or at elevated temperature up to the reflux temperature of the reaction mixture. Generally, the reaction takes place at a temperature in the range from 10° to 150° C.

An excess of the sodium alcoholate (preferably 1.5-2-fold) and or an excess of the acetamide is advantageous. The latter can be recovered and fed into the reaction again.

The process according to the invention may be used to prepare all the compounds of general formula I but it is particularly useful for compounds of formula I wherein in group A:
$R_1$ is $C_{1-4}$-alkoxy, $C_{1-4}$-alkyl, or amino
$R_2$ is $C_{1-4}$-alkoxy, $C_{1-4}$-alkyl or halogen
$R_3$ is hydrogen or halogen in group B:
$R_4$ is hydrogen or halogen
$R_5$ is hydrogen, phenyl or halophenyl
X is a single bond or $-O-$
and Q represents a morpholine group wherein $R_8$ and $R_9$ are both hydrogen. The halogen or halo-substituent may be a fluorine, chlorine, bromine or iodine atom but is preferably a chlorine or bromine atom.

In the group A the substitution in the phenyl ring is preferably in the 3 and 4 positions or in the 3, 4 and 5 positions, particularly preferred examples of such substitution being 3,4-dimethoxy, 3-ethoxy-4-methoxy, 3-chloro-4-methoxy, 3-bromo-4-methoxy, 3-methyl-4-methoxy, 3-ethyl-4-methoxy, 3-propyl-4-methoxy, 3,4-dimethyl, 3-amino-4-methoxy, 3,5-dichloro-4-amino and 3-methoxy-4-methyl. Of these, 3,4-dimethoxy substitution of the phenyl ring is especially preferred.

The process according to the invention is further illustrated by the following Examples.

EXAMPLE 1

3-(4-Chlorophenyl)-3-(3,4-dimethoxyphenyl)acrylic acid morpholide

4-Chloro-3',4'-dimethoxy benzophenone (6.29 g, 25 mmol), sodium tert.-amylate (5.50 g, 50 mmol), acetyl morpholine (23.90 g, 185 mmol), and anhydrous toluene (50 ml) were stirred under reflux for 8 hours. After cooling, the solution was washed twice with water, dried, and the toluene distilled off on a rotary evaporator. The viscous residue was stirred at 50° C. with diisopropyl ether (40 ml), whereupon the substance solidified. After it had cooled to room temperature, the crude product was crushed, filtered by suction, washed with diisopropyl ether (2×5 ml) and dried.

Yield: 8.1 g=83.5% of theoretical Tlc-pure product.

EXAMPLE 2

3-[4-(4-Chlorophenoxy)phenyl]-3-(3,4-dimethoxyphenyl)acrylic acid morpholide

Sodium hydride (with 20% of paraffin oil; 2.25 g, 75 mmol) was stirred under reflux with absolute toluene (50 ml) and tert.-amyl alcohol (7.25 g, 82.5 mmol) was added dropwise within 30 minutes. When the solution had cooled to 100° C., 4-(4-chlorophenoxy)-3',4'-dimethoxy benzophenone (9.22 g, 25 mmol) and acetyl morpholine (16.17 g, 125 mmol) were added and the mixture was stirred under reflux for 8 hours.

After cooling to room temperature the solution was washed with water (2×100 ml), dried and applied onto a column packed with silica gel (50 g). The products were eluted with toluene (200 ml) and toluene-acetone mixtures (200 ml each; 90:10, 80:20, 70:30). The fractions containing the substance with an Rf-value of 0.47 (toluene-acetone 70:30) were combined and concentrated on a rotary evaporator. Crude yield: 11 g of viscous oil which contains toluene. This oil was stirred with diisopropyl ether (30 ml), whereupon the desired compound slowly crystallised.

Yield: 8.7 g=72.5% of theoretical
mp.: 115°-127° C.
Isomer ratio E/Z: 45/55.

EXAMPLE 3

3-(4-Chlorophenyl)-3-(3,4-dimethoxyphenyl)acrylic acid morpholide

Sodium hydride (with 20% of paraffin oil; 3.0 g, 100 mol) was stirred with absolute toluene (70 ml) and a solution of tert.-butanol (8.15 g, 110 mmol) in absolute toluene (30 ml) was added dropwise. After the solution had cleared, 4-chloro-3',4'-dimethoxy benzophenone (13.84 g, 50 mmol) and acetyl morpholine (19.37 g, 150 mmol) were added and the reaction mixture was refluxed for 8 hours with stirring. When the solution had cooled to room temperature, it was washed twice with water, dried and concentrated on a rotary evaporator.

Thereby 24.9 g of viscous oil were obtained which crystallised slowly upon stirring in diisopropyl ether (50 ml). Recrystallisation from isopropanol/diisopropyl ether.

Yield: 19.0 g=92.8% of theoretical
m.p.: 123°-145° C.

We claim:

1. A process for the preparation of a 3,3-diaryl acrylic acid amide of general formula I

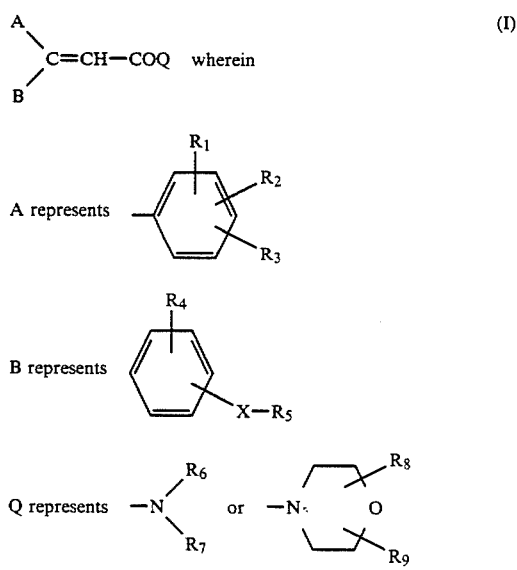

in which
$R_1$ is $C_{1-4}$-alkyl, $C_{1-4}$-alkoxy, $NH_2$, $NHC_{1-4}$-alkyl, $N(C_{1-4}$-alkyl$)_2$, $C_{3-4}$-alkenyl, $C_{3-4}$-alkynyl, $C_{3-4}$ alkenyloxy, $C_{3-4}$-alkynyloxy, or $C_{3-6}$-cycloalkyl;
$R_2$ is $C_{1-4}$-alkyl, $C_{1-4}$-alkoxy or halogen;
$R_3$ is hydrogen or halogen;
$R_4$ is hydrogen, halogen, $C_{1-4}$-alkyl or $C_{1-4}$-alkoxy;
$R_5$ is hydrogen, a phenyl group optionally substituted by one or more substituents selected from $C_{1-4}$-alkyl, $C_{1-4}$-alkoxy and halogen moieties, a $C_{1-12}$ alkyl group optionally substituted by one or more halogen atoms, a $C_{3-7}$-cycloalkyl, phenylphenyl, or phenoxyphenyl group, a $C_{2-6}$-alkenyl or $C_{2-6}$-alkynyl group each optionally-substituted by a phenyl group, or a naphthyl or $C_{5-8}$-cycloalkenyl group;
X is a single bond, —O—, —S(O)$_p$—, —N=N—, —CHR$_9$O—, —OCHR$_9$—, —CHR$_9$S(O)$_p$—, —S(O)$_p$CHR$_9$— —(CH$_2$)$_n$—, —HC=CH—, or —C≡C—;
$R_6$ is $C_{1-4}$-alkyl, $C_{3-7}$-cycloalkyl, benzyl, $C_{3-4}$-alkenyl or $C_{3-4}$-alkynyl;
$R_7$ is $C_{1-4}$ alkyl;
$R_8$ is hydrogen, $C_{1-4}$-alkyl or $C_{1-4}$-alkoxy;
$R_9$ is hydrogen or $C_{1-4}$-alkyl;
p is 0, 1 or 2; and
n is an integer from 1 to 10
provided that when X is —N=N— $R_5$ is other than hydrogen by reacting a benzophenone of formula II

in which A and B have the meanings given above, with an acetamide of formula III $$CH_3COQ \qquad (III)$$

in which Q has the meaning given above, in the presence of a base characterised in that the base employed is a sodium tertiary alcoholate.

2. A process according to claim 1 characterised in that the sodium tertiary alcoholate is derived from an alcohol of general formula IV $$(R)_3C-OH \qquad (IV)$$

wherein each R is independently an alkyl group of 1 to 4 carbon atoms.

3. A process according to claim 1 characterised in that the sodium tertiary alcoholate is derived from amyl alcohol or butyl alcohol.

4. A process according to any one of claims 1 to 3 characterised in that excess sodium alcoholate is present.

5. A process according to any one of claims 1 to 3 characterised in that the acetamide of formula III is present in excess.

6. A process according to any one of claims 1 to 3 characterised in that an inert solvent is employed.

7. A process according to any one of claims 1 to 3 wherein the reaction temperature is in the range from 10° to 150° C.

* * * * *